US009951135B2

(12) United States Patent
Possani Postay et al.

(10) Patent No.: US 9,951,135 B2
(45) Date of Patent: Apr. 24, 2018

(54) MONOCLONAL ANTIBODIES AGAINST THE DEC-205 RECEPTOR OF CHICKEN DENDRITIC CELLS

(71) Applicant: UNIVERSIDAD NACIONAL AUTÓNOMA DE MÉXICO, Distrito Federal (MX)

(72) Inventors: Lourival Domingos Possani Postay, Morelos (MX); María Martha Pedraza Escalona, Morelos (MX); Gerardo Pavel Espino Solis, Durango (MX); Alejandro Olvera Rodríguez, Morelos (MX); Héctor Miguel Cardoso Torres, Morelos (MX)

(73) Assignee: UNIVERSIDAD NACIONAL AUTÓNOMA DE MÉXICO, Distrito Federal (MX)

( * ) Notice: Subject to any disclaimer, the term of this patent is extended or adjusted under 35 U.S.C. 154(b) by 18 days.

(21) Appl. No.: 14/898,037

(22) PCT Filed: Jun. 17, 2014

(86) PCT No.: PCT/MX2014/000093
§ 371 (c)(1),
(2) Date: Dec. 11, 2015

(87) PCT Pub. No.: WO2014/209096
PCT Pub. Date: Dec. 31, 2014

(65) Prior Publication Data
US 2016/0347841 A1 Dec. 1, 2016

(30) Foreign Application Priority Data
Jun. 26, 2013 (MX) .................... MX/a/2013/007474

(51) Int. Cl.
C07K 16/28 (2006.01)
A61K 39/145 (2006.01)
C12N 7/00 (2006.01)
A61K 47/68 (2017.01)
A61K 39/00 (2006.01)

(52) U.S. Cl.
CPC ........ *C07K 16/2851* (2013.01); *A61K 39/145* (2013.01); *A61K 47/6833* (2017.08); *A61K 47/6849* (2017.08); *C12N 7/00* (2013.01); *A61K 2039/505* (2013.01); *A61K 2039/552* (2013.01); *C12N 2760/16131* (2013.01)

(58) Field of Classification Search
None
See application file for complete search history.

(56) References Cited

U.S. PATENT DOCUMENTS

| | | |
|---|---|---|
| 8,236,318 B2 | 8/2012 | Keler et al. |
| 8,362,214 B2 | 1/2013 | Keler et al. |
| 8,586,720 B2 | 11/2013 | Keler et al. |
| 2004/0146948 A1 | 7/2004 | Britton et al. |
| 2004/0258688 A1 | 12/2004 | Hawiger et al. |
| 2006/0281672 A1 | 12/2006 | Hart et al. |
| 2009/0130109 A1 | 5/2009 | Hart et al. |
| 2009/0175880 A1 | 7/2009 | Keler et al. |
| 2010/0098704 A1 | 4/2010 | Keler et al. |
| 2010/0303819 A1 | 12/2010 | Hart et al. |
| 2012/0276049 A1 | 11/2012 | Stern et al. |
| 2012/0309031 A1 | 12/2012 | Keler et al. |
| 2013/0101593 A1 | 4/2013 | Keler et al. |

FOREIGN PATENT DOCUMENTS

| | | |
|---|---|---|
| EP | 2 570 137 A2 | 3/2013 |
| WO | 2004/035619 A1 | 4/2004 |
| WO | 2004/053138 A1 | 6/2004 |
| WO | 2011/044452 A2 | 4/2011 |

OTHER PUBLICATIONS

W.J. Swiggard, et al.; "DEC-205, a 205-kDa Protein Abundant on Mouse Dendritic Cells and Thymic Epithelium That Is Detected by the Monoclonal Antibody NLDC-145: Purification, Characterization , and N-Terminal Amino Acid Sequence"; Cellular Immunology; 1995; pp. 302-311; vol. 165.
International Search Report issued in Application No. PCT/MX2014/000093, dated Dec. 1, 2014.
Kato Masato et al, "Expression of human DEC-205 (CD205) multilectin receptor on leukocytes" .International Immunology (2006), vol. 18, No. 6 Pags: 857-869.

*Primary Examiner* — Jennifer E Graser
(74) *Attorney, Agent, or Firm* — Studebaker & Brackett PC

(57) ABSTRACT

The invention relates to the production and the characterization of new murine monoclonal antibodies that recognize the domain CTDL-2 (SEQ ID NO: 1) of the cell receptor DEC-205 of dendritic cells in chickens (*Gallus gallus*), pigs, (*Sus scrofa*) and humans (*Homo sapiens*). The invention also relates to the capacity of the new antibodies to direct and modulate the immune response at different levels in chickens (*Gallus gallus*) and pigs (*Sus scrofa*), as well as recognizing the receptor DEC-205 in dentritic cells and cell lines in humans. In addition, the invention is used to quickly produce a specific humoral immune response against Hemaglutinina H5 of the H5N2-type avian flu virus.

15 Claims, 8 Drawing Sheets

A

Homo sapiens    Sus scrofa

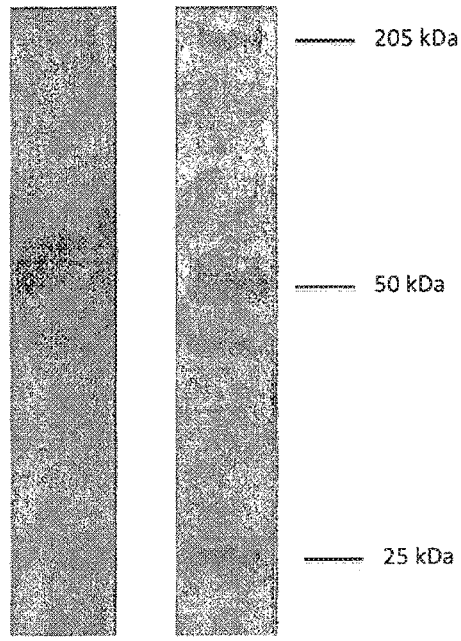

— 205 kDa

— 50 kDa

— 25 kDa

B

Figure 1:
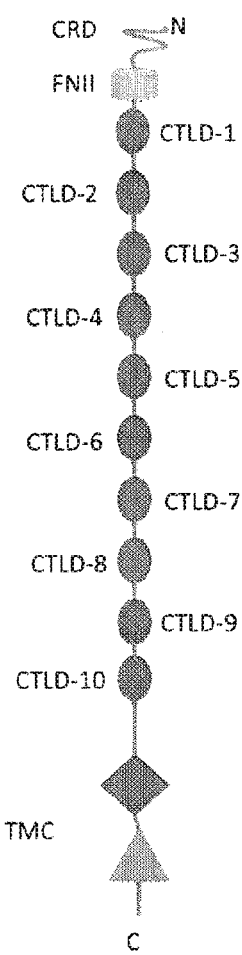

```
ref|NP_001032925.1|  351  EFWRHVNTRCDAG-WLPHNGFCYMLIHNQASWSTADQLCKANKSNLISIHSLADVELIVT  409
ref|NP_001171875.1|  352  DVWTYSDTRCDAADWLPNDGFCYLLVNESDSWDKAHMKCKTFSSDLISIHSLADVEVIVT  411
ref|NP_002340.2|     352  DVWTYSDTRCDAG-WLPNNGFCYLLVNESNSWDKAHAKCKAFSSDLISIHSLADVEVVVT  410
                          :.* : :*****. ***:;****.*:::. **,.*. **; ,*;*************;:**

ref|NP_001032925.1|  410  KLHN-DAREEVWVGLRNEDVPTLFKWSDRTDVVFTYWDQNEPSVPFNATPNCVSYSGKLG  468
ref|NP_001171875.1|  412  KLHKGDAKEETWTGLRNVNTPTLFQWSDGTEVTLTYWNENEPNVPYNKTPNCVSYLGKLG  471
ref|NP_002340.2|     411  KLHNEDIKEEVWIGLKNINIPTLFQWSDGTEVTLTYWDENEPNVPYNKTPNCVSYLGELG  470
                          ***: * ;**.* **:* ; ****;*** *;*.;***;;***.**;* ******* *;.**

Ident.
ref|NP_001032925.1|  469  QWRVKSCEENLKYVCKKKGKILNETKSDKNCSLDE  503
ref|NP_001171875.1|  472  QWKVQSCEEKLKYVCKKKGEKLNDTRSDKMCPPDE  506     65%
ref|NP_002340.2|     471  QWKVQSCEEKLKYVCKRKGEKLNDASSDKMCPPDE  505     65%
                          **;*;****;******;**;  **;  *** *.  **
```

Fig. 10

SEQUENCE LISTING

<160> NUMBER OF SEQ ID NOS: 25

<210> SEQ ID NO 1
<211> LENGTH: 153
<212> TYPE: PRT
<213> ORGANISM: Gallus gallus

<400> SEQUENCE: 1

```
Glu Phe Trp Arg His Val Asn Thr Arg Cys Asp Ala Gly Trp Leu Pro
1               5                   10                  15

His Asn Gly Phe Cys Tyr Met Leu Ile His Asn Gln Ala Ser Trp Ser
            20                  25                  30

Thr Ala Asp Gln Leu Cys Lys Ala Asn Lys Ser Asn Leu Ile Ser Ile
        35                  40                  45

His Ser Leu Ala Asp Val Glu Leu Ile Val Thr Lys Leu His Asn Asp
    50                  55                  60

Ala Arg Glu Glu Val Trp Val Gly Leu Arg Asn Glu Asp Val Pro Thr
65                  70                  75                  80

Leu Phe Lys Trp Ser Asp Arg Thr Asp Val Val Phe Thr Tyr Trp Asp
                85                  90                  95

Gln Asn Glu Pro Ser Val Pro Phe Asn Ala Thr Pro Asn Cys Val Ser
            100                 105                 110

Tyr Ser Gly Lys Leu Gly Gln Trp Arg Val Lys Ser Cys Glu Glu Asn
        115                 120                 125

Leu Lys Tyr Val Cys Lys Lys Lys Gly Lys Ile Leu Asn Glu Thr Lys
    130                 135                 140

Ser Asp Lys Asn Cys Ser Leu Asp Glu
145                 150
```

<210> SEQ ID NO 2
<211> LENGTH: 34
<212> TYPE: DNA
<213> ORGANISM: Gallus gallus

<400> SEQUENCE: 2
catgccatgg agttttggag acacgtgaat actc                          34

<210> SEQ ID NO 3
<211> LENGTH: 59
<212> TYPE: DNA
<213> ORGANISM: Gallus gallus

<400> SEQUENCE: 3
gagacccacc cacacttctt ctctggcatc attatgaagt ttcgtcgtaa caatgagtt    59

<210> SEQ ID NO 4
<211> LENGTH: 27
<212> TYPE: DNA
<213> ORGANISM: Gallus gallus

<400> SEQUENCE: 4
gccagagaag aagtgtgggt gggtctc                                  27

<210> SEQ ID NO 5
<211> LENGTH: 36
<212> TYPE: DNA
<213> ORGANISM: Gallus gallus

<400> SEQUENCE: 5
gactctccac tgccccaact tgcctgaata ggacac                        36

<210> SEQ ID NO 6
<211> LENGTH: 18
<212> TYPE: DNA
<213> ORGANISM: Gallus gallus

<400> SEQUENCE: 6
ggggcagtgg agagtcaa                                                    18

<210> SEQ ID NO 7
<211> LENGTH: 54
<212> TYPE: DNA
<213> ORGANISM: Gallus gallus

<400> SEQUENCE: 7
cccaagcttg ggttaatgat gatgatgatg atgctcatcc aatgagcaat tttt           54

<210> SEQ ID NO 8
<211> LENGTH: 586
<212> TYPE: PRT
<213> ORGANISM: Influenza A virus

<400> SEQUENCE: 8

```
Asp Tyr Asp Ile Pro Thr Thr Glu Asn Leu Tyr Phe Gln Gly Ala Met
1               5                   10                  15

Gly Ser Gly Ile Glu Arg Ile Cys Arg Ile Arg Leu Met Glu Arg Ile
            20                  25                  30

Val Ile Ala Phe Ala Ile Ile Ser Ile Val Thr Gly Asp Gln Ile Cys
        35                  40                  45

Ile Gly Tyr His Ala Asn Asn Ser Thr Lys Gln Val Asp Thr Ile Met
    50                  55                  60

Glu Lys Asn Val Thr Val Thr His Ala Gln Asp Ile Leu Glu Lys Glu
65                  70                  75                  80

His Asn Gly Arg Leu Cys Ser Leu Lys Gly Val Lys Pro Leu Ile Leu
                85                  90                  95

Lys Asp Cys Ser Val Ala Gly Trp Leu Leu Gly Asn Pro Met Cys Asp
            100                 105                 110

Glu Phe Leu Asn Val Pro Glu Trp Ser Tyr Ile Val Glu Lys Asp Asn
        115                 120                 125

Pro Ala Asn Gly Leu Cys Tyr Pro Gly Asn Phe Asn Tyr Tyr Glu Glu
    130                 135                 140

Leu Lys His Leu Met Ser Ser Thr Asn His Phe Glu Lys Ile Gln Ile
145                 150                 155                 160

Phe Pro Arg Ser Ser Trp Ser Asn His Asp Ala Ser Ser Gly Val Ser
                165                 170                 175

Ser Ala Cys Pro Tyr Asn Gly Arg Ser Ser Phe Phe Arg Asn Val Val
            180                 185                 190

Trp Leu Ile Lys Lys Asn Asn Val Tyr Gln Thr Ile Lys Arg Thr Tyr
        195                 200                 205

Asn Asn Thr Asn Val Glu Asp Leu Leu Ile Leu Trp Gly Ile His His
    210                 215                 220

Pro Asn Asp Ala Ala Glu Gln Ile Lys Leu Tyr Gln Asn Pro Asn Thr
225                 230                 235                 240

Tyr Val Ser Val Gly Thr Ser Thr Leu Asn Gln Arg Ser Ile Pro Glu
                245                 250                 255

Ile Ala Thr Arg Pro Lys Val Asn Gly Gln Ser Gly Arg Met Glu Phe
            260                 265                 270
```

-continued

```
Phe Trp Thr Ile Leu Arg Pro Asn Asp Ser Ile Thr Phe Glu Ser Thr
            275                 280                 285
Gly Asn Phe Ile Ala Pro Glu Tyr Ala Tyr Lys Ile Ile Lys Lys Gly
290                 295                 300
Asp Ser Ala Ile Met Lys Ser Glu Leu Asn Tyr Gly Asn Cys Asp Ala
305                 310                 315                 320
Lys Cys Gln Thr Ser Val Gly Ala Ile Asn Ser Ser Met Pro Phe His
                325                 330                 335
Asn Val His Pro Phe Thr Ile Gly Glu Cys Pro Lys Tyr Val Lys Ser
                340                 345                 350
Lys Lys Leu Val Leu Ala Thr Gly Leu Arg Asn Val Pro Gln Arg Glu
            355                 360                 365
Thr Arg Gly Leu Phe Gly Ala Ile Ala Gly Phe Ile Glu Gly Gly Trp
            370                 375                 380
Gln Gly Met Val Asp Gly Trp Tyr Gly Tyr His His Ser Asn Glu Gln
385                 390                 395                 400
Gly Ser Gly Tyr Ala Ala Asp Lys Glu Ser Thr Gln Lys Ala Ile Asp
                405                 410                 415
Gly Ile Thr Asn Lys Val Asn Thr Ile Ile Asp Lys Met Asn Thr Gln
                420                 425                 430
Phe Glu Ala Val Gly Lys Glu Phe Asn Asn Leu Glu Arg Arg Ile Glu
            435                 440                 445
Asn Leu Asn Lys Lys Met Glu Asp Gly Phe Ile Asp Val Trp Thr Tyr
            450                 455                 460
Asn Ala Glu Leu Leu Val Leu Met Glu Asn Glu Arg Thr Leu Asp Leu
465                 470                 475                 480
His Asp Ser Asn Val Lys Asn Leu Tyr Asp Lys Val Arg Leu Gln Leu
                485                 490                 495
Arg Asp Asn Ala Lys Glu Leu Gly Asn Gly Cys Phe Glu Phe Tyr His
                500                 505                 510
Arg Cys Asp Asp Lys Cys Met Glu Ser Val Arg Asn Gly Thr Tyr Asp
            515                 520                 525
Tyr Pro Gln Tyr Ser Glu Glu Ser Arg Leu Asn Arg Gly Glu Ile Asp
            530                 535                 540
Gly Val Lys Leu Glu Ser Met Gly Thr Tyr Gln Ile Leu Ser Ile Tyr
545                 550                 555                 560
Ser Thr Val Ala Ser Ser Leu Ala Leu Ala Ile Met Ile Ala Gly Gln
                565                 570                 575
Ala Glu Phe Gln His Thr Gly Gly Arg Tyr
            580                 585
```

<210> SEQ ID NO 9
<211> LENGTH: 21
<212> TYPE: DNA
<213> ORGANISM: Influenza A virus

<400> SEQUENCE: 9
cattcggctt taaaattgtc c                                              21

<210> SEQ ID NO 10
<211> LENGTH: 20
<212> TYPE: DNA
<213> ORGANISM: Influenza A virus

<400> SEQUENCE: 10

-continued caccatccta atgatgcggc                                                      20

<210> SEQ ID NO 11
<211> LENGTH: 20
<212> TYPE: DNA
<213> ORGANISM: Influenza A virus

<400> SEQUENCE: 11
atggaaagaa tagtgattgc                                                      20

<210> SEQ ID NO 12
<211> LENGTH: 20
<212> TYPE: DNA
<213> ORGANISM: Influenza A virus

<400> SEQUENCE: 12
gaccagctat catgattgcc                                                      20

<210> SEQ ID NO 13
<211> LENGTH: 112
<212> TYPE: PRT
<213> ORGANISM: Mus musculus

<400> SEQUENCE: 13

Asp Ile Val Met Ser Gln Ser Pro Ser Ser Leu Ala Val Ser Ala Gly
1               5                   10                  15

Glu Arg Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Arg Ala Glu Asp Leu Ala Val Tyr Tyr Cys Lys Gln
                85                  90                  95

Ser Tyr Asn Leu Tyr Thr Phe Gly Arg Gly Thr Lys Leu Glu Ile Lys
            100                 105                 110

<210> SEQ ID NO 14
<211> LENGTH: 112
<212> TYPE: PRT
<213> ORGANISM: Mus musculus

<400> SEQUENCE: 14

Glu Ile Val Leu Thr Gln Ser Ile Ala Ser Leu Thr Val Ser Ala Gly
1               5                   10                  15

Glu Arg Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 15
<211> LENGTH: 113
<212> TYPE: PRT
<213> ORGANISM: Mus musculus

<400> SEQUENCE: 15

```
Glu Val Gln Leu Gln Gln Ser Thr Ala Glu Phe Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Arg Tyr Asp Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Asp Val Thr Tyr Trp Gly Gln Gly Thr Leu Val Thr Val
            100                 105                 110

Ser
```

<210> SEQ ID NO 16
<211> LENGTH: 113
<212> TYPE: PRT
<213> ORGANISM: Mus musculus

<400> SEQUENCE: 16

```
Glu Val Gln Leu Gln Gln Ser Gly Ala Asp Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Arg Tyr Asp Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Asp Val Thr Tyr Trp Gly Gln Gly Thr Leu Val Thr Val
            100                 105                 110

Ser
```

<210> SEQ ID NO 17
<211> LENGTH: 24
<212> TYPE: DNA
<213> ORGANISM: Artificial Sequence
<220> FEATURE:
<223> OTHER INFORMATION: Synthesized

<400> SEQUENCE: 17
gcwgghgaga gsgtyacyat gagc        24

<210> SEQ ID NO 18
<211> LENGTH: 18
<212> TYPE: DNA

```
<213> ORGANISM: Artificial Sequence
<220> FEATURE:
<223> OTHER INFORMATION: Synthesized

<400> SEQUENCE: 18
tcagaggaag gtggaaac                                                    18

<210> SEQ ID NO 19
<211> LENGTH: 22
<212> TYPE: DNA
<213> ORGANISM: Artificial Sequence
<220> FEATURE:
<223> OTHER INFORMATION: Synthesized

<400> SEQUENCE: 19
gtgtcagcag gasaragggt ca                                               22

<210> SEQ ID NO 20
<211> LENGTH: 18
<212> TYPE: DNA
<213> ORGANISM: Artificial Sequence
<220> FEATURE:
<223> OTHER INFORMATION: Synthesized

<400> SEQUENCE: 20
acactcattc ctgttgaa                                                    18

<210> SEQ ID NO 21
<211> LENGTH: 23
<212> TYPE: DNA
<213> ORGANISM: Artificial Sequence
<220> FEATURE:
<223> OTHER INFORMATION: Synthesized

<400> SEQUENCE: 21
gaggtbcarc tkcarcartc tac                                              23

<210> SEQ ID NO 22
<211> LENGTH: 17
<212> TYPE: DNA
<213> ORGANISM: Artificial Sequence
<220> FEATURE:
<223> OTHER INFORMATION: Synthesized

<400> SEQUENCE: 22
gcagaryttg tgcarcc                                                     17

<210> SEQ ID NO 23
<211> LENGTH: 20
<212> TYPE: DNA
<213> ORGANISM: Artificial Sequence
<220> FEATURE:
<223> OTHER INFORMATION: Synthesized

<400> SEQUENCE: 23
tacatatgca aggcttacaa                                                  20

<210> SEQ ID NO 24
<211> LENGTH: 20
<212> TYPE: DNA
<213> ORGANISM: Artificial Sequence
<220> FEATURE:
<223> OTHER INFORMATION: Synthesized

<400> SEQUENCE: 24
gcgtaatacg actcactata                                                  20
```

```
<210> SEQ ID NO 25
<211> LENGTH: 21
<212> TYPE: DNA
<213> ORGANISM: Artificial Sequence
<220> FEATURE:
<223> OTHER INFORMATION: Synthesized

<400> SEQUENCE: 25
ctcactaaag ggaacaaaag c                                              21
```

MONOCLONAL ANTIBODIES AGAINST THE DEC-205 RECEPTOR OF CHICKEN DENDRITIC CELLS

TECHNICAL SCOPE

This invention pertains to the production and characterization of new murine monoclonal antibodies that recognize the CTLD-2 domain (SEQ ID NO: 1) of the DEC-205 cellular receptor of dendritic cells in chickens (*Gallus gallus*), pigs (*Sus scrofa*), and humans (*Homo sapiens*). This invention pertains to producing new monoclonal antibodies from hybridomas that are created by fusing SP2 myeloma cells with spleen cells of BALB/c rats that have been immunized with the CTLD-2 (SEQ ID NO: 1) fragment of avian origin of this receptor. The invention also pertains to the capability of the new antibodies to direct and significantly modulate the immune response at different levels in chickens (*Gallus gallus*) and pigs (*Sus scrofa*), as well as to recognize the DEC-205 receptor in dendritic cells and cell lines of human origin. In addition, there is a brief description of the application of this invention in obtaining a specific humoral immune response over the short term against hemagglutinin H5 (SEQ ID NO: 8) of the H5N2 avian flu virus.

BACKGROUND TO THE INVENTION

The immune system has highly specialized cells for carrying out various processes; among them dendritic cells (DCs) have the ability to stimulate the primary and secondary responses of the B and T lymphocytes, as well as the response of T cytotoxic lymphocytes in rats and human lymphocytes (Carter et al., 2006). This capability is due to the fact that DCs are the cells that are most highly specialized in the presentation of antigens, internalizing, processing, and presenting them in the form of peptides combined with the molecules of the major histocompatibility complex class II (MHC-II). They originate from the myeloid progenitor cells, which are capable of differentiating themselves into immature dendritic cells and ultimately into mature dendritic cells by expressing various surface markers. The function as an antigen present or of dendritic cells has been connected to high levels in the expression of the DEC-205 receptor, also called CD205 or lymphocytic antigen 75, especially in dendritic cells located in areas of T cells of peripheral or secondary lymph organs (Jiang et al., 1995; Kraal et al., 1986; Winter-Pack et al., 1995). This was substantiated by the internalization of human anti-DEC-205 receptor dendritic cells (Bonifaz et al., 2002; Steinman and Banchereau, 2007; Steinman, 2008; Ueno et al., 2010). The DEC-205 receptor is an endocytic receptor with a broad extracellular domain that contains various subdomains: a cysteine-rich (CR) domain, a fibronectin type II (FN) domain and 10 contiguous carbohydrate recognition domains (CRDs), also known as C-type lectin domains (or CTLDs in the English acronym) (Mahnke et al., 2000). These multi-lectin domains affect the efficiency of the processing and presentation of antigens in vivo (Hawiger et al., 2001). Other examples of C-type lectin receptors include Langerina, DC-SIGN, mannose receptor and $A_2$ phospholipase receptor, which have also been implicated in antigen processing and presentation (Figdor et al., 2002; Idoyaga et al., 2008).

It should be noted that the pioneering experiments that described the cellular processes of directing an antigen were carried out using the DEC-205 human receptor, where the T-cell-mediated response changes dramatically when the maturation stimulus of the dendritic cells is added at the same time as the directing of the antigen using an antibody directed against the DEC-205 receptor (Bonifaz et al., 2002; Hawiger et al., 2001). The proliferation of T cells increases by various orders of magnitude when compared to a classic immunization protocol. It has also been observed that, when the antigens are directed at the dendritic cells via DEC-205, there is an increase in the stimulation of the cooperating T cells (Th); this makes it possible or promotes the humoral immune response or antibody production (Bonifaz et al., 2004; Boscardin et al., 2006). In point of fact, the directing of antigens using this marker and CD11c has increased the kinetics of the production of high-titer antibodies during the first seven days after immunization (Wang et al., 2000; Cheong et al., 2010). Moreover, the presence of the DEC-205 receptor has been described in lines other than human dendritic cells, such as in B cells, T cells, NK cells, and monocytes (Kato et al., 2006); cerebral capillaries, stroma of the medulla ossea, and cortical epithelium of the thymus; they are also found in other species of mammals such as chimpanzees and rats and in other non-mammalian species (Kraal et al., 1986; Witmer-Pack et al., 1995), including chickens (*Gallus gallus*).

DEC-205 Receptor of *Gallus gallus*

The genome and protein sequences for the DEC-205 receptor of *Gallus gallus* has been reported in the European Nucleotide Archive (http://www.ebi.ac.uk/ena/, access number AJ574899; in the ENSEMBL database (http://www.ensembl.org/), in the GenBank (http://www.ncbi.nlm.nih.gov), access number NP_001032925.1), and in the UniProtKB/TrEMBL, where it has access number Q4LDF5. These databases report the presence of 35 exons that have codifying sequences; these make up the domains of the DEC-205 receptor of chickens, represented as N-CRD-FNII-CTLD1-CTLD2-CTLD3-CTLD4-CTLD5-CTLD6-CTLD7-CTLD8-CTLD9-CTLD10-TMC, where N is the N-terminal region, CRD represents the cysteine-rich domain, FNII represents the type II fibronectin domain, CTLD1 to CTLD10 represent the 10 "type-C lectin domains", and TMC represents the transmembrane and cytoplasmic domains (FIG. 1).

In recent years investigation into dendritic cells has been focused mainly on the application of new clinical procedures, in particular the implementation of new tools that enhance the immune response within short periods of time.

Antibodies

The use of antibodies or immunoglobulins that recognize the surface receptors of dendritic cells is based on the ability of these molecules to interact in a specific manner and with high affinity for the immunogens against which they are produced. The antigens are glycoproteins that comprise two heavy chains and two light chains that are interconnected by disulfide bridges to an antigen union region. The heavy chains have a variable region ($V_H$) and a constant region ($C_H$), with the latter being able to present 3-4 domains, which intervene directly in the union with cells of the immune system or with the complement system (Padlan, 1994). However, the light chains comprise a variable region ($V_L$) and a constant region which has a single domain $C_L$. The variable regions ($V_H$ and $V_L$) contain the antigen union site, referred to as hypervariability regions or complementarity-determining regions (CDR). These regions are interspersed with more conservative regions that are called marker or "framework" regions (FR).

The antibodies that exhibit a high degree of union specificity and affinity for an epitope are the monoclonal antibodies, which are produced by a hybridoma that is generated by the fusion of immortalized cells (myeloma), which do not secrete immunoglobulins, and B cells obtained from the spleens of rats immunized against an antigen that contains the information of the heavy and light chains.

Combined with monoclonal interbody technology, in the state of the art, it is possible to obtain the genes that codify the variable domains of all possible immunoglobulins by rearranging the nucleotide sequences. This can be obtained from the lymphocytes of any vertebrate, including human beings. In reality, right now it is possible to select only the variable elements of the heavy and light chains of the antibodies, which can be united by a connector peptide in such a way as to produce a fragment of a single chain of the antibodies, which are able to recognize the antigens. Our group was able to prepare a bank of genes that express the single-chain fragments and, by means of the filamentous-phage deployment technique, it was possible to obtain antibodies that protect against toxins of scorpion venom (Riaño-Umbarilla et al., 2005, see also U.S. Pat. No. 7,381,802 B2, Jun. 3, 2008). An idea that underlies these advances in the technique and is complementary to this invention is to obtain single-chain fragments of human antibodies for the purpose of applying the same principle as described here, against possible antigens that cause health problems in humans (Rodriguez-Rodriguez et al., 2012). In other words, the idea is to obtain by genetic engineering the variability in single chains of human antibodies for possible application in the development of vaccines.

BRIEF DESCRIPTION OF THE FIGURES

FIG. 1 depicts in schematic form the different domains of the DEC-205 receptor; the latter belongs to the type C family of lectins. In the amino-terminal region (N) is the cysteine-rich domain (CRD), followed by a fibronectin domain type II (FNII) and 10 "type C lectin domains" (CTLD-1 to CTLD-10). In the carboxyl-terminal region the transmembrane and cytoplasmic (TMC) domains are represented.

FIG. 2 shows the expression vector (pET22b) indicating various loci that are present, as well as the location of the CTLD-2 gene. A: His-Tag; B: stop codon; and C: origin of F1.

FIG. 3 shows some of the steps in the process of purification of the CTLD-2 domain in 12% SDS gel electrophoresis.

FIG. 4 A) shows the titer of the polyclonal serum of two rats that were immunized with the CTLD-2 recombinant immunogen, compared to pre-immune polyclonal serum. The logarithm of the dilution is plotted on the abscissa, and absorbency at 405 nm is plotted on the ordinate; (a): pre-immune serum; (b): serum from rat 1 and (c) serum from rat 2. B) shows a graphic of the union of the two anti-CTLD-2 murine antibodies using supernatant from the hybridomas obtained by the indirect ELISA technique. On the abscissa are the different hybridomas obtained, and absorbency at 405 nm is plotted on the ordinate. C): shows the recognition of the monoclonal antibodies 2F2E8E3B4, 2F2E8E3B6, 4D12R, and 4D12F4 toward the CTLD-2 domain by indirect ELISA. On the abscissa are the various monoclones obtained, and on the ordinate absorbency at 405 nm is plotted.

FIG. 5 shows the titer of the monoclonal antibody 2F2E8E3B6 compared to the supernatant of the SP2 cells. The dilution logarithm is plotted on the abscissa, and absorbency at 405 nm is plotted on the ordinate; (a): AbM 2F2E8E3B6, and (b): supernatant of the SP2 cells.

FIG. 6 shows the immunoprecipitation of lysed cells of chicken (*Gallus gallus*) spleen using the anti-CTLD-2 murine monoclonal antibodies. The specific immune-isolation of the DEC-205 receptor (205 kDa) present in white chicken spleen cells in a gel SDS-PAGE at 10% under reduction conditions compared to a negative control (left-hand track) is observed. The electrophoretic run of the heavy chain (50 kDa) and light chain (25 kDa) of the 2F2E8E3B6 antibody is also observed. Con: Control.

FIG. 7 shows the internalization of the chicken DEC-205 receptor using the anti-CTLD-2 antibodies in the cell line of T lymphocytes (Jurkat) using intracellular staining analyzed by flow cytometry. 7A shows the control, and 7B shows the cells after 30 minutes of incubation with the anti-CTLD-2 antibody; on average a percentage of 13.91% of the cells that internalize the white of the antibody is observed. Co: count, and (a): PE cells.

FIG. 8 shows the titers of IgY with respect to avian hemagglutinin H5, monitored by Western Blot.

FIG. 9 shows the titers of IgY with respect to avian hemagglutinin H5 after intradermal immunization of two hens. The IgYs obtained from the yolks of the eggs 15, 18, and 21 days after immunization are compared to the IgYs of control hens. The dilution logarithm is plotted on the abscissa, and absorbency at 405 nm is plotted on the ordinate. G1: hen 1; G2: hen 2; (a): preimmune serum; (b): 15 days; (c): 18 days; and (d): 21 days.

FIG. 10 A) shows the recognition of the lymphocytic receptor 75 (DEC-205) in species other than *Gallus gallus*, such as *Homo sapiens* (human) and *Sus scrofa* (pig) by means of immunoprecipitation using the anti-CTLD-2 antibody 2F2E8E3B6. B) shows the alignment of sequences of the CTLD-2 segment 2F2E8E3B6 of the lymphocytic antigen 75 of *Gallus gallus* (NP_001032925.1) compared to the sequences of *Homo sapiens* (NP_002340.2) and the pig (*Sus scrofa*) (NP_001171875.1), as well as their percentage of identity.

DETAILED DESCRIPTION OF THE INVENTION

This invention provides new monoclonal antibodies of murine origin that are capable of recognizing the DEC-205 receptor of *Gallus gallus*, which has properties that are particular and specific to the immunological level in dendritic cells. Thus, the antibodies that are produced have the potential to be used in a variety of directed immunologic processes, such as affecting the ability to present different antigens, inducing the response of T cells, or increasing the proportion of antibodies produced against a variety of specific avian pathogens. Various aspects of the invention are described in detail in the following sections.

Definitions

The expressions "cell" and "cell culture" as used here are employed as synonyms, and all of these designations include offspring. Thus, the words "transformants" and "transformed cells" include the primary subject cell and cultures derived therefrom without considering the number of transfers. It is also understood that not all offspring have to be exactly identical with regard to their DNA content due to deliberate or accidental mutations. This includes mutant offspring that have the same function or biological activity as that detected in the originally transformed cell. When different designations are intended, these should be clear from the context.

The term "effective quantity" or "pharmacologically effective quantity" of a compound in a single dose of the mixture depends on various factors. These factors include the amounts of other ingredients in the case where they are used and tolerance to the active ingredient of the compound.

"Pharmaceutically acceptable vehicle" refers to the filler or diluent solids or liquids or substances that can be safely used when administered systemically or topically. Depending on the particular pathway of administration, various vehicles that are well known in the industry and that include filler or diluent solids or liquids, hydrotropes, surfactants, and encapsulating substances are pharmaceutically acceptable. The amount of vehicle used along with the monoclonal antibodies provides a manageable dose of material per single dose of the compound.

Pharmaceutically acceptable vehicles for systemic administration that can be incorporated into the compound of the invention include sugar, starches, cellulose, vegetable oils, buffers, polyols, and alginic acid. Specific pharmaceutically acceptable vehicles are described in the following documents, all of which are mentioned here as references: U.S. Pat. No. 4,401,663, Buckwalter et al., granted on Aug. 30, 1983; European Patent Application number 089710, LaHann et al., published on Sep. 28, 1983, and European Patent Application number 0068592, Buckwalter et al., published on Jan. 5, 1983. The vehicles that are preferred for parenteral administration are polypropylene glycol, pyrrolidine, ethyl oleate, aqueous ethanol, and combinations thereof.

Representative vehicles include gum arabic, agar, alginates, hydroxyalkyl cellulose, hydroxypropyl methyl cellulose, carboxymethyl cellulose, sodium carboxymethyl cellulose, carrageenan, powdered cellulose, guar gum, cholesterol, gelatin, gum agar, gum arabic, karaya gum, gum ghatti, locust bean gum, octoxynol-9, oleyl alcohol, pectin, polyacrylic acid and its homologues, polyethylene glycol, polyvinyl alcohol, polyacrylamide, sodium lauryl sulfate, polyethylene oxide, polyvinylpyrrolidine, glycol monostearate, propylene glycol monostearate, gum xanthan, tragacanth, sorbitan esters, stearic alcohol, and starch and modifications thereof. The adequate ranges vary from 0.5% to 1%.

1. Immunogens of DEC-205
   Using homology modeling (with the EsyPred3D and SWISS-MODEL Repository programs) of all of the domains of DEC-205 and taking as molds structures of the homolog domains previously reported (www.pdb.org), the domains that had greater exposure to the solvent, as well as the sites that were involved in the union to ligands in the structure of chicken DEC-205 (Jiang et al. 1995), were located. The domains that were selected to be cloned and expressed in a heterologous system were the following:
   1. Cysteine-rich domain (CRD, cysteine rich domain), located in the amino-terminal region of the extracellular side of the DEC-205 receptor (see FIG. 1).
   2. Fibronectin (FN) type II domain, located in the amino-terminal region of the extracellular side of the DEC-205 receptor (see FIG. 1).
   3. Type C lectin-like domain 2 (CTLD-2, C-Type Lectin-Like Domain-2), located on the extracellular side of the DEC-205 receptor and involved in the union with carbohydrates (Jiang et al. 1995) (see FIG. 1).
   To carry out the cloning of these fragments, the introns and exons of the genes of each of the domains selected were analyzed using the Wise2 program (http://www.ebi.ac.uk/Tools/Wise2/index.html) and the Artemis program (http://www.sanger.ac.uk/resources/software/artemis/). Of the three domains selected, only the CTLD-2 domain was cloned and expressed satisfactorily in large quantities.

Figure 2:
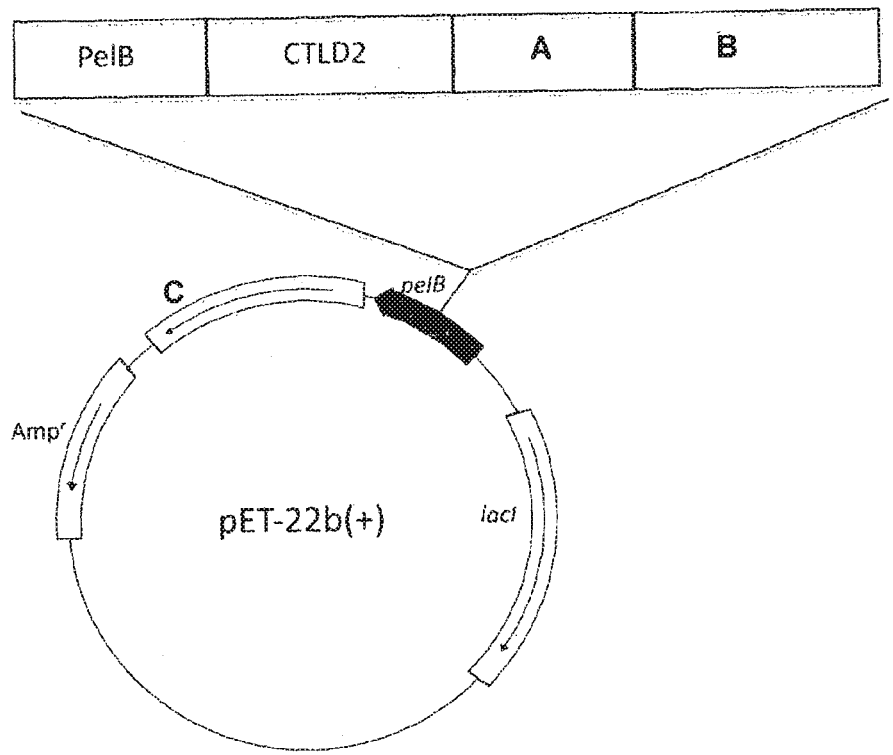
Figure 3:
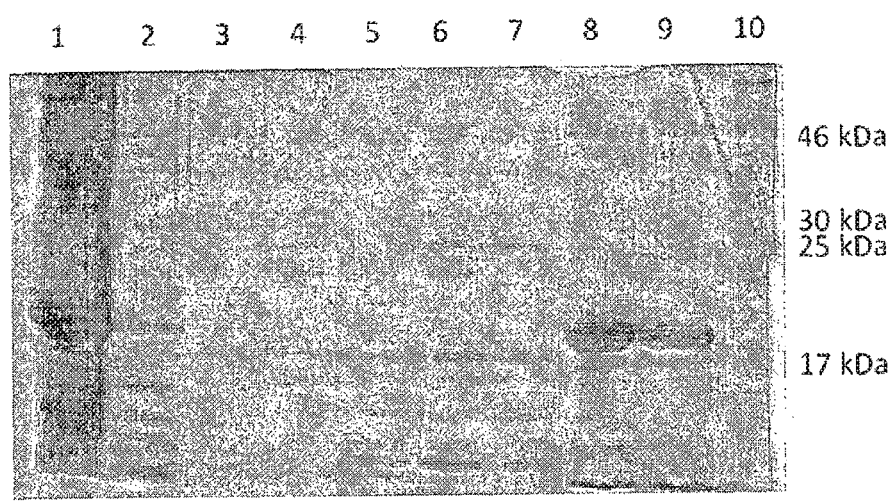

2. Cloning and Expression of the CTLD-2 Domain
   This invention undertakes the recombinant production of the CTLD-2 domain of the DEC-205 receptor of *Gallus gallus*, the domain selected as an immunogen for generating monoclonal antibodies because it provided easier access for foreign molecules since it is located on the extracellular surface of the DEC-205 receptor and cloning and recombinant expression thereof proved to be satisfactory. For this purpose, using genomic DNA obtained from the peripheral blood of a healthy chicken, the exons of this domain were isolated with the specific oligos CTLD-E1FNco, CTLD-E1R, CTLD-E2F, CTLD-E2R, CTLD-E3F, CTLD-E3RHin (SEQ ID NO: 2, 3, 4, 5, 6, and 7, respectively), and they were then assembled, cloned in the pET-22b(+) vector (FIG. 2), and transformed for recombinant expression thereof in the Rosetta II strain of *E. coli*. After they were expressed, they were purified (FIG. 3) and characterized in order to be used as an immunogen, as detailed in Example 1.

3. Immunization of BALB/c Rats with the Recombinant CTLD-2 Domain
   The immunization with the CTLD-2 recombinant domain was done intraperitoneally (IP) by administering to five rats increasing concentrations of antigen (25, 50, 100, 150, and 200 µg) with a complete Freund adjuvant at a ratio of 1:1 (100 µL total volume), followed every 10 days by IP administration of the antigen alternatingly mixed with incomplete adjuvant or alumina (at a ratio of 1:1) (up to a total of five immunizations). The immune response was monitored during the immunization protocol by taking samples of murine serum obtained from the retro-orbital complex during the fourth immunization. These samples were analyzed by the indirect ELISA method (FIG. 4A), where the rats with high titers of anti-DEC-205 chicken antibodies were used to fuse with the immortalized spleen cells. The rats were reinforced by IP with antigen one or two days before they were sacrificed and their spleens were removed.

4. Generation and Production of the Antibodies that Recognize DEC-205
   This invention undertakes to generate murine monoclonal antibodies that are capable of recognizing the DEC-205 receptor of *Gallus gallus* via the CTLD-2 domain (SEQ ID NO. 1). The monoclonal antibodies that were united with DEC-205 with high recognition included those produced by a hybridomas of the 4D12 and 2F2 families (FIG. 4B), which were produced as shown in detail in Example 2, in accordance with well-standardized protocols (Koehler and Milstein, 1975; Goding, 1986).
   After the hybridomas were identified as producers of the antibodies with the desired specificity, sub-cloning was done by limiting dilution and growth in the D-MEM medium under standard conditions (Goding, 1986). In cases where four monoclones, 2F2E8E3B4, 2F2E8D3B6, 4D12R, and 4D12F4 presented high recognition for the CTLD-2 domain, which was identified by the indirect ELISA method (FIG. 4C) [translator's note: incomplete sentence]. The isotypes of the monoclonal antibodies obtained were determined by sandwich ELISA using the culture supernatants of the hybridomas and the commercial Mouse Typer Sub-Isotyping kit (Bio Rad). In addition, the hybridomas were grown in vivo inducing liquid tumors (ascites) in various rats of the BALB/c strain in order to produce sufficient quantities of antibodies.

The monoclonal antibodies secreted by the hybridomas were separated from the ascitic fluid and from the growth medium by conventional procedures for purification of immunoglobulins such as affinity chromatography using Protein A-Sepharose, as illustrated in Example 3. The ones in which greater yields were obtained during the purification process were selected for the purpose of determining their $EC_{50}$ (FIG. 5), and the sequencing of the variable light and heavy chains of these antibodies was then done (Example 12).

5. Functional Characterization of the Anti-DEC-205 Monoclonal Antibodies

Figure 6:
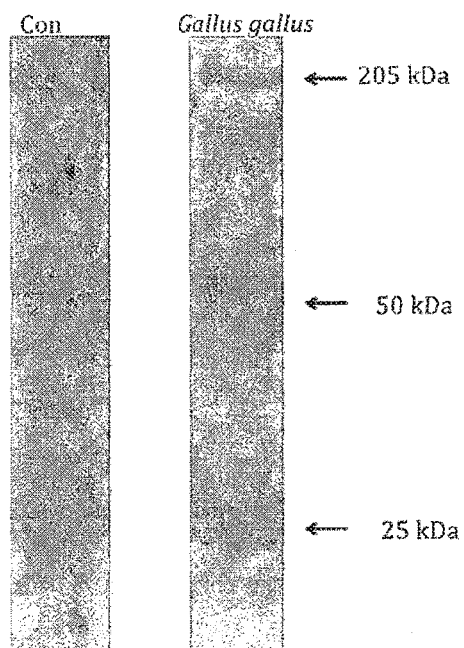

In order to determine whether the anti-CTLD-2 monoclonal antibodies unite with the DEC-205 receptor as expressed in live cells of *Gallus gallus* and other species and whether these antibodies make it possible for the receptor to operate in the internalization and processing of antigens the techniques of flow cytometry and immunoprecipitation were used, as illustrated in Examples 5, 6, and 10. For instance, use was made of the clear lysates of white cells that had been previously purified from various organs and various cell lines in which the presence of the DEC-205 receptor was determined by the immunoprecipitation technique, using the monoclonal antibody with greater recognition as determined by this invention, 2F2E8E3B6, at saturating concentrations. After incubation was done with the primary antibody, a second phase was carried out in which the Sepharose-Protein A resin (Pierce, Rockford, Ill., USA) was added; this complex made the antibody insoluble once united with the protein A, making it possible to separate the antibody with its specific target by centrifuging and to analyze this interaction by SDS-PAGE. As an example of this, FIGS. 6 and 10A are presented in which the presence of a band at 205 kDa is observed that is approximately recognized by the monoclonal antibodies produced in this work, indicating the presence of the DEC-205 receptor in the spleen cells of *Gallus gallus* and *Sus scrofa* and in cell lines of *Homo sapiens*. On the other hand, using cellular preparations in which the presence of the DEC-205 receptor and monoclonal antibodies of the 2F2 anti-CTLD-2 monoclonal antibodies was identified, an analysis was made of the internalization of these antibodies via their target by determining the presence of these antibodies, located intracellularly, using flow cytometry (Example 6, FIG. 7). In the case of the antibodies that were used, their presence was observed inside the cells that were used, confirming the process of internalization.

6. Obtaining Hemagglutinin 5 from the H5N2 Avian Flu Virus

This invention used the RNA of the type H5N2 avian flu virus obtained from a collection of RNAs donated by Dr. R. Webster (St. Jude Hospital, Tennessee, USA) in order to isolate the gene that contains the hemagglutinin H5 (SEQ ID. NO: 8), the antigenic determining principal for developing the pathogenesis of the flu virus, as well as cloning and expressing it heterologically using the baculovirus system, which is described in Example 7.

7. Molecular Conjugates with the Monoclonal Antibodies

The possibility of obtaining a very wide variety of molecular conjugates that are generally based on an antigen united with the monoclonal antibodies of the present invention that are capable of recognizing the DEC-205 receptor that is present in chicken antigen presenting cells (CPA) [translator's note: incomplete sentence]. This makes it possible to direct the antigen to the CPAs to step up the processing, presentation, and immune response against the antigen, for example, the release of immuno-stimulating cytokines or an increase in the humoral response. These anti-CTLD-2 antibodies can be united with cells or pathogens by means of chemical "linkers" or by any other related method such as those described by Kruif et al., 2000, and Nizard et al., 1998. In Example 8 a description is given of the conjugation or coupling procedure used. Briefly, the monoclonal antibodies were activated with succinimidyl-4-(N-maleimidomethyl) cyclohexane-1-carboxylate (SMCC; Pierce, Rockford, Ill., USA), which adds maleimide and ester groups to the proteins that make covalent conjugation possible with molecules that contain sulfhydryl or amino groups, while the antigen used, the recombinant protein of hemagglutinin H5 (SEQ. ID NO:8) of the avian flu virus was modified with 2-iminothiolane (Traut, Pierce, Rockford, Ill., USA), which is reactive and which reacts with primary amines to introduce sulfhydryl groups at these sites, generating target sites for the modified antibodies and carrying out covalent conjugation, as detailed in Example 8.

Figure 9:
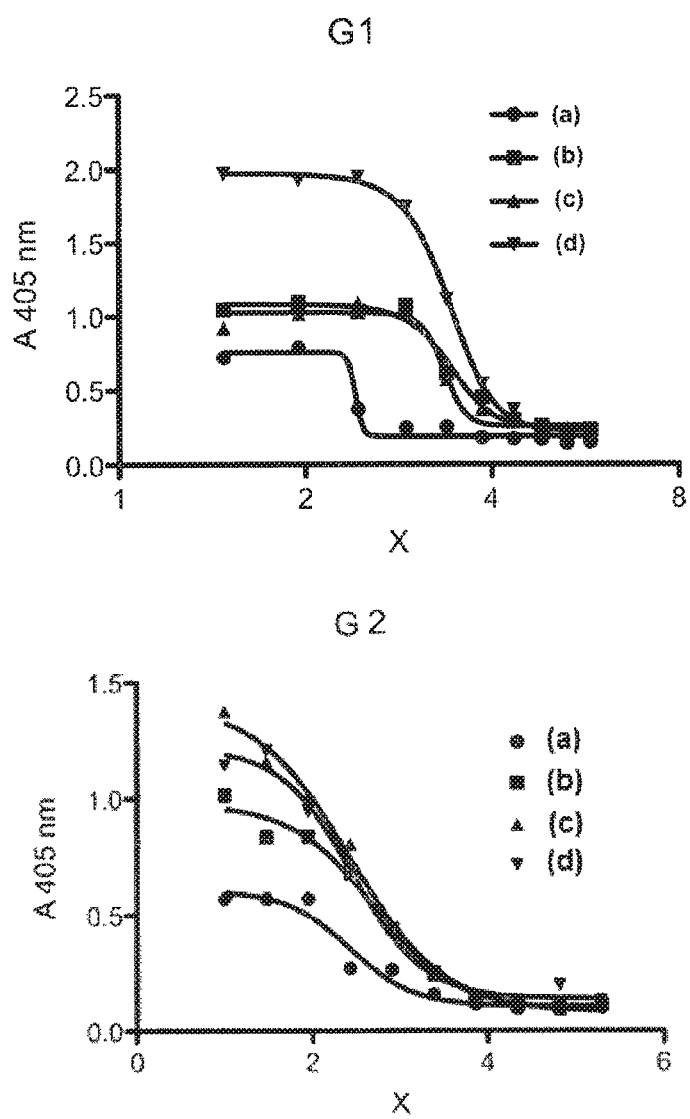

8. Effect Analysis in the Immune Response in Birds from the Immunization of the Molecular Conjugate Anti-DEC-205 Antibodies-H5 Hemagglutinin To carry out this analysis, two egg-laying hens of the Rhode Island Red type, 25 weeks old, were immunized with the Ab 2F2E8D3B6-Hemagglutinin H5 conjugate mixture. Then IgYs were purified from the egg yolks in order to determine the titers of the Hemagglutinin H5 (SEQ. ID NO:8) chicken antibodies (IgYs) by means of indirect ELISA (see Example 9). The hens successfully generated antibodies that were capable of recognizing the viral protein with larger titers compared to the control starting at day 15 (FIG. 9), confirming that the anti-CTLD-2-Hemagglutinin H5 conjugates of this invention have the potential to be used to generate an effectively rapid immune response with the generation of antibodies that protect against possible viral infections.

9. Uses of the Invention

The proposal of this invention extends to veterinary uses, especially for fattening chickens and egg-laying hens using the species *Gallus gallus* as a model, due to the fact that the movement of these specimens from production areas to consumption areas can form foci for the spread of contagious diseases. This proposal uses the DEC-205 receptor of *Gallus gallus* as a modulator of the immune response since the molecules that specifically recognize dendritic cells by means of this receptor, as specific antibodies directed against the complete protein or one of its domains, have the potential to direct the immune response at different levels and to produce a potent immune response against the antigens that are united with these antibodies, by means of chemical conjugation or genetic engineering. It is thus possible to speed up the immune response against innumerable specific infections among these birds.

The molecular conjugates of this invention have the ability to be used to treat or prevent a variety of diseases and/or specific conditions in the species *Gallus gallus* and in animals in which there exists cross-reactivity in recognition by means of this receptor. The viral antigen-antibody conjugates can be used to prevent viral illnesses such as avian smallpox, Newcastle disease, coronavirus, enterovirus, etc. Likewise, bacterial antigen-antibody conjugates can be used to prevent bacterial illnesses such as avian cholera or infectious coryza. For example, using the Cp39 protein of *Pasteurella multocida* for the case of avian cholera (Sthitmatee et al., 2008) or the protein of the HMTp210 external membrane (210 kDa) of *Avibacterium paragallinarum*, which produces infectious coryza (Sakamoto et al., 2012) [translator's note: incomplete sentence]. Likewise, some viral agents that cause cancer in this species of animal can be used as antigens to make the conjugates, for example, the gp85 protein of the subgroup J avian leukosis virus (Sun et al., 2012).

Among these diseases, the highly pathogenic avian flu seriously affects poultry farmers wherever it presents, with the always-present possibility of a pandemic, which would be devastating both to the economy and to the populace. As a recent example, in 2012 there was an avian flu outbreak in our country that caused significant economic losses to Mexican aviculture. This invention used Hemagglutinin H5, the principal antigenic determinant of the H5N2 avian flu, as an antigen that was directed by the new antibodies of this invention produced against domain 2 of type-C lectins of DEC-205 (anti-CTLD-2) upon being conjugated with them.

For use in therapy, the conjugates of this invention may be administered to patients indirectly, for example, by first growing or incubating the conjugates with antigen presenter cells, such as dendritic cells, and then administering them to the patients (ex vivo) (Gunzer and Grabbe, 2001; Steinman, 1996; Tacken et al., 2006; Tacken et al., 2007). In all cases the conjugates are administered in quantities that are sufficient to achieve their desired therapeutic effect, for example, to eliminate the bacterial, viral, or fungal infection. The effective quantity for each particular application may vary depending on the illness or condition to be treated. The preferred pathways for administering the conjugates include, for example, subcutaneous or intraperitoneal injection or possibly oral administration if necessary.

EXAMPLES

The following examples are presented by way of illustrating some of the methods for obtaining or utilizing this invention. It is possible to implement many variations on these methods without exceeding the scope of this invention, and therefore they should not be considered limiting in any way.

Example 1

Cloning, Expression, and Purification of the CTLD-2 Domain (SEQ ID NO:1)

The amino-acid sequence of the DEC-205 receptor of *Gallus gallus* is reported in GenBank (http://www.ncbi.nlm.nih.gov) with access number NP_001032925. 1. In the list of sequences, the CTLD-2 domain that was cloned is presented as SEQ ID NO:1, which was obtained from genomic DNA of the peripheral blood of a healthy chicken using specific oligos CTLD-E1FNco, CTLD-E1R, CTLD-E2F, CTLD-E2R, CTLD-E3F, and CTLD-E3RHin (SEQ ID NO: 2, 3, 4, 5, 6, and 7, respectively) to obtain the three exons that comprise them, which were assembled, cloned, and transformed to provide for their recombinant expression in the Rosetta-II strain of *E. coli*. FIG. 2 shows in detail the cloning site of CTLD-2 with in the expression vector pET22b(+), which is flanked by the pelB sequence in the amino-terminal region, which directs the recombinant protein toward the bacterial periplasm, in addition to a contiguous sequence of six histidines in the carboxyl-terminal region that are used for its purification, and finally a stop line is attached. This system was optimum for expression in inclusion bodies of recombinant protein CTLD-2 (SEQ ID NO:1) after being induced with IPTG to a final concentration of 0.2 mM once a $DO_{600\ nm}$ of 0.7 was reached. After 12 hours of induction, the cellular precipitate was obtained, which was solubilized under denaturing conditions (a buffer of phosphate-TrisHCl, pH 8.0, and 8M of urea), ensonified, and centrifuged. The soluble fraction containing the protein of interest was purified by affinity chromatography using a nickel-NTA-agarose column (Qiagen, USA), with elution being done by changing the pH. FIG. 3 shows some of the steps in the process of the purification of the CTLD-2 domain by affinity chromatography (SEQ ID NO:1) in SDS-PAGE electrophoresis at 12%, stained with colloidal coomassie. Traces: 1) precipitate solubilized in a buffer of phosphate-TrisHCl, pH 8.0, and 8M of urea; 2) first washing with 4M of urea; 3) with 2M of urea; 4) with 0.2M of urea; 5) washing with 25 mM of imidazole; 6) elution 1 with 250 mM of imidazole; 7) elution 2 with 250 mM of imidazole; 8) elution at pH 5.9; 9) elution at pH 4.5; 10) molecular weight markers (Pre-stained Protein Marker Broad Range, New England, Biolabs). Then, the samples that were eluted by changing pH 4.5 were reduced with DTT (Sigma Aldrich, USA), 100 mM for one hour at 52° C., then undergoing a second step of purification by phase-reverse HPLC using a $C_{18}$ preparation column (Vydac, USA) in a Waters 600E apparatus equipped with an absorbency detector within the ultraviolet (UV) light spectrum, Waters 486 and a Waters 745B graph plotter, with a linear gradient of 20-70% of acetonitrile in the presence of 0.1% trifluoroacetic acid (TFA) at a flow rate of 1.60 mL/minute for a period of 50 minutes, in which the CTLD-2 peak was obtained at a retention time of 33.74. This material, which was subjected to analysis by mass spectrometry, showed that it was homogeneous and had a molecular weight of 21,229 Da, indicating that the domain was united with the signal peptide in accordance with the construct shown in FIG. 2. The concentration of the CTLD-2 protein (SEQ ID NO:1) was determined from the molar extinction coefficient, which was theoretically estimated with the ProtParam server (http://ca.expasy.org/tools/protparam.html). Following this purification protocol, a yield of 1.0 mg of protein of 98% purity was obtained per liter of culture.

Example 2

Generation of Hybridomas that Produce Murine Monoclonal Antibodies Toward DEC-205

In order to generate hybridomas that produce monoclonal antibodies toward DEC-205 of *Gallus gallus*, five rats were immunized intraperitoneally with the CTLD-2 domain (SEQ ID NO:1) with increasing concentrations of antigen (25, 50, 100, 150, and 200 μg) with a complete Freund adjuvant at a ratio of 1:1, followed every 10 days with IP immunizations of the antigen mixed alternatingly with incomplete adjuvant or alumina (ratio 1:1) (up to a total of five immunizations). After the last immunization, the murine splenocytes were isolated and fused in the presence of 50% PEG (w/v) to an immortal cell line, in this case the SP2 rat myeloma cell line. The fused cells were placed in 96-well plates at 37° C. at 5% $CO_2$ in 100 μl of a selective HAT medium (Sigma Aldrich, USA); at 48 hours, 100 μL of HT medium was added in order to reduce the concentration of aminopterin with respect to the volume of the culture; after 10 days of growth, the wells were observed where hybridomas had grown and replacement was done with the selective HT medium (Sigma Aldrich, USA). Once extensive growth of the hybridomas had been verified, a sample was taken consisting of 100 μL of the growth medium, and an evaluation was done of the production of murine IgG antibodies that were specific against the CTLD-2 domain by means of the indirect ELISA technique. The results are shown in FIG. 4A, which shows the eight hybridomas with greater recognition by means of ELISA toward the CTLD-2 domain (SEQ ID NO:1); of these, the murine antibodies produced by the 2F2 and 4D12 hybridomas were the ones that exhibited the highest level of recognition by indirect ELISA.

Figure 4:
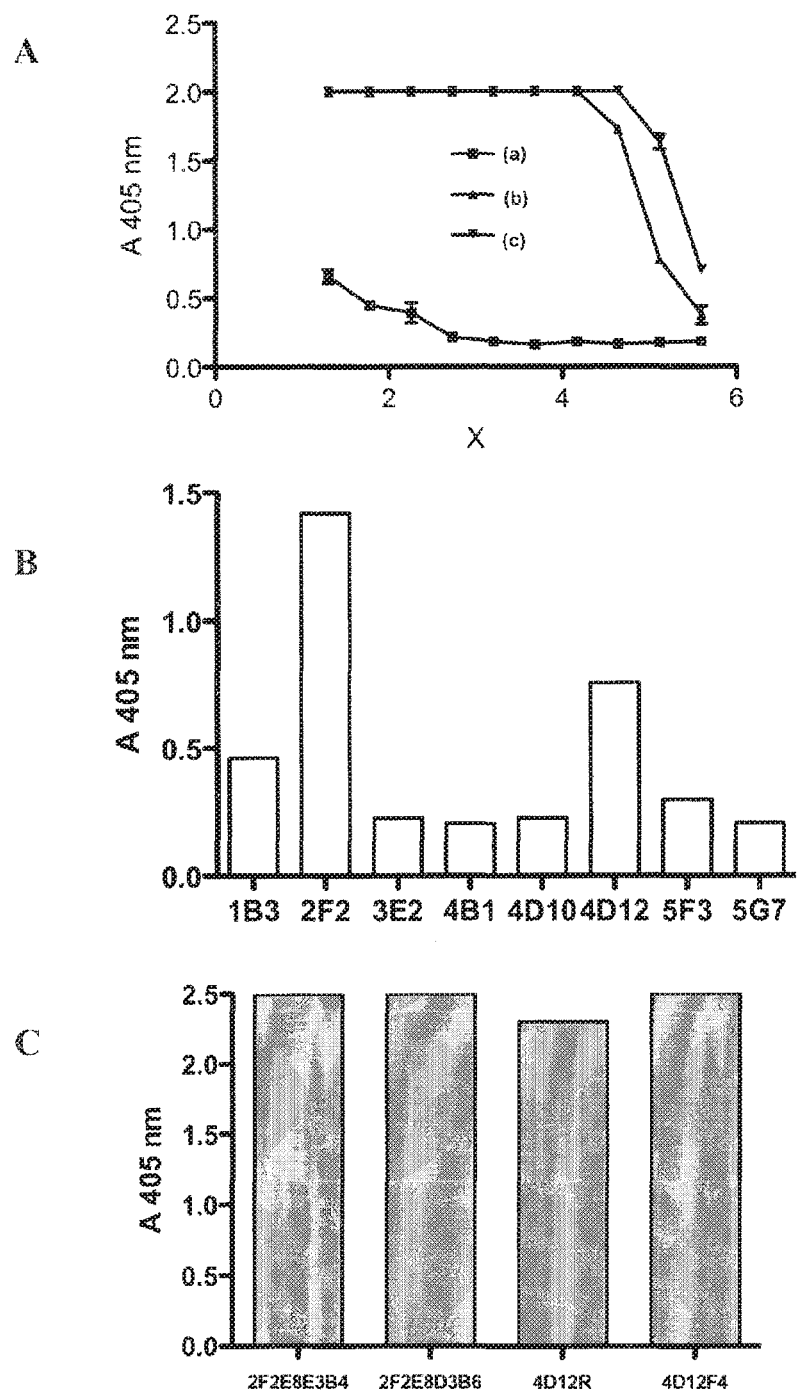

These antibody-secreting hybridomas (2F2 and 4D12) were expanded, reevaluated, and subcloned at least three or four times by limiting dilution. The results are shown in FIG. 4B, which shows that the 2F2E8E3B4, 2F2E8D3B6, 4D12R, and 4D12F4 monoclones had the highest levels of union for the CTLD-2 antigen (SEQ ID NO:1) by indirect ELISA.

Example 3

Production and Purification of Anti-DEC-205 Murine Monoclonal Antibodies

The 2F2E8E3B4, 2F2E8D3B6, 4D12R, and 4D12F4 monoclones were cultivated in vivo in a DMEM medium (Hyclone Laboratories, Thermal Fisher Scientific, USA) with 10% inactivated bovine fetal serum (Byproducts, Mexico), OPI (Sigma Aldrich, USA), and antibiotics (streptomycin/penicillin, Sigma Aldrich, USA) in order to generate antibodies in the supernatant, and they were then characterized and purified. Likewise, in vivo induction of ascitic fluid was done upon inducing liquid tumors by means of intraperitoneal administration of the above-mentioned monoclones in BALB/c rats that were previously stimulated with Pristano (Sigma Aldrich, USA). After a period of 15-20 days, the hybridomas were inoculated, and 8-10 days later the ascitic fluid was milked and kept frozen for subsequent purification and characterization.

The monoclonal antibodies secreted by the hybridomas were separated from the growth medium or ascitic fluid by conventional immunoglobulin purification procedures such as affinity chromatography using Protein A-Sepharose (Pierce, Rockford, Ill., USA). In the case of the clones grown in a growth medium, they were expanded in 75 cm$^2$ flat-bottom bottles. The supernatants were filtered, concentrated, and dialyzed against PBS before being purified by affinity chromatography and eluted by pH change using 100 mM of ascitic acid pH 3.0. All of the elution samples were received in Tris 1M pH 8.0 buffer in order to be neutralized. The concentration of protein was determined by $DO_{280\ nm}$ using an extinction coefficient of 1.43. The immunoglobulin purification process was verified by SDS-PAGE and ELISA.

Example 4

Characterization of the Monoclonal Antibodies Toward DEC-205 by Indirect ELISA

Figure 5:
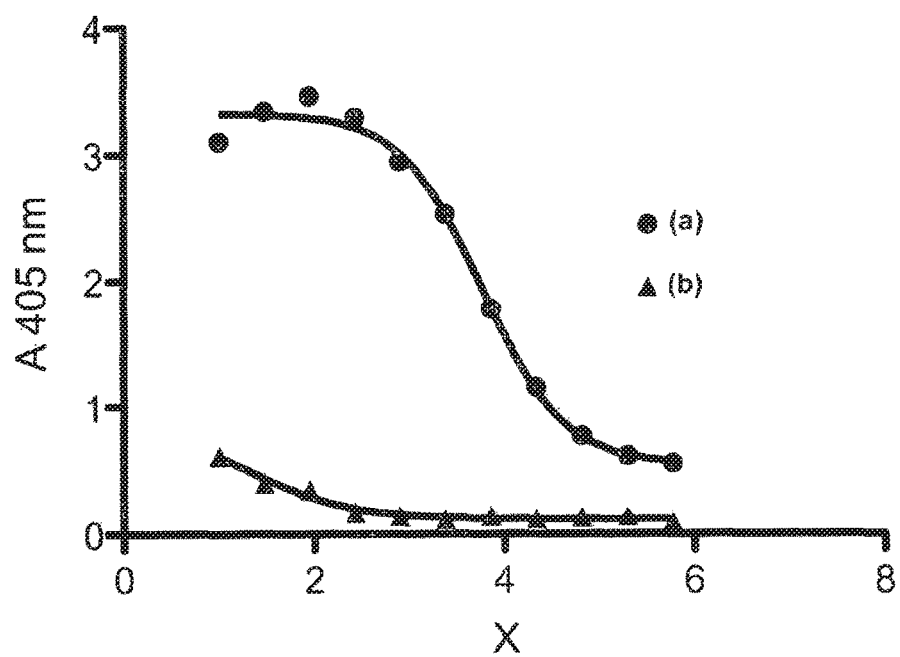

100 μL/well of the CTLD-2 recombinant antigen (SEQ ID NO:1) was placed in 96-well high-union polystyrene plates, expressed as in Example 1 at a concentration of 3 μg/mL in 50 mM of carbonate buffer and incubated over night at 4° C. The plates were blocked with 5% bovine serum albumin in Tris 50 mM pH 8.0 and with 0.2% Tween 20 for one hour at 37° C. After washing was done three times with a wash solution (Tris 50 mM pH 8, NaCl 150 mM, 0.05% Tween), incubation was done at 37° C. for one hour with serial dilutions of the monoclonal antibodies that were produced and purified as described in Example 3. After the washing operation was repeated, incubation was done for one hour at 37° C. with the secondary anti-rat goat antibody coupled to HRP (1:5000, Zymed Laboratories Incorporated). The ABTS substrate (2,2'-azino-di(3-ethyl-benzothiazoline)sulfonate) (Roche Applied Science, Germany) was used in the revealing process. The reading in units of absorbency was done at 405 nm in the ELISA Tecan Spectra reader. Supernatant from the Sp2 cellular culture was used as a negative control. FIG. 5 shows the titration curve of the 2F2E8E3B6 purified antibody which was done in triplicate, producing an $EC_{50}$ of 4.4 ng, while the 4D12R had an $EC_{50}$ of 1.377 μg; therefore the 2F2E8E3B6 antibody turned out to have greater recognition for the CTLD-2 domain.

The isotypes of the monoclonal antibodies that were obtained were determined by sandwich ELISA using the supernatants from the hybridomas and the commercial kit Mouse Typer Sub-Isotyping Kit (BioRad, Calif., USA) following the vendor's instructions. The antibodies of the 2F2 family have a heavy chain with the IgG2a isotype and a lambda-type light chain, while the antibodies of the 4D12 family have a heavy chain with the IgG1 isotype and a kappa-type light chain.

Example 5

Immunoprecipitation with Anti-CTLD-2 Antibodies

White cells of the spleens of chickens (*Gallus gallus*), four weeks old, were stimulated with lipopolysaccharide (LPS, SIGMA Aldrich USA) 200 ng/mL, for 24 hours and were then lysed in an immunoprecipitation buffer (PBS pH 7.4, 1% Triton X-100 with protease inhibitor). The supernatant from this lysate was incubated with 2F2 anti-DEC-205 monoclonal antibodies for 16 hours at 4° C. while being stirred. Subsequently 30 μL of protein A-Sepharose (Pierce Rockford, Ill., USA) was used for immunoprecipitation, incubating for one hour at ambient temperature. The immune complexes that were formed were washed exhaustively with PBS-Tween 0.1%. The immunoprecipitates were eluted by boiling for five minutes in a sample buffer with SDS. The results are shown in FIG. 6, where the specific immunoisolation of the DEC-205 receptor (205 kDa) from cells present in the chicken spleen in a 10% SDS-PAGE gel under reduction conditions was observed, and the heavy chain (50 kDa) and the light chain (25 kDa) of the 2F2E8E3B6 antibody was observed with which immunoprecipitation was carried out. The molecular weights are indicated. This result indicates that the antibodies generated in this invention recognize the DEC-205 receptor that is present in the chicken (*Gallus gallus*) spleen cells based on the recognition of the CTLD-2 domain (SEQ ID NO:1).

Example 6

Internalization Test

Figure 7:
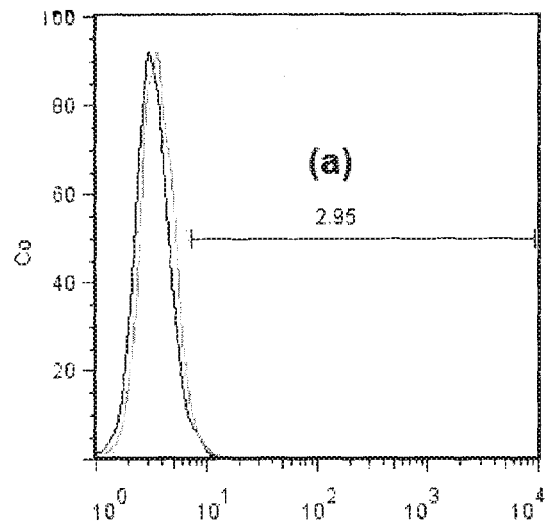
Figure 7:
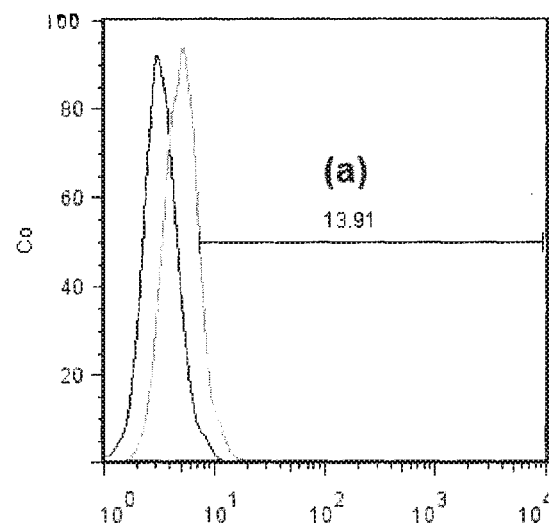

The multi-lectin domains affect the efficiency of in vivo antigen processing and presentation; an indirect way of evaluating this process is to measure the internalization of anti-CTLD2 antibodies (SEQ ID NO:1) by the dendritic cells isolated from chicken spleens and by Jurkat cells. In general, 1×10E6 cells were stimulated with LPS for 24 hours and were then harvested, washed with PBS, and resuspended in 100 μL of 4% p-formaldehyde for 15 minutes at ambient temperature. After a second washing with PBS, resuspension was done in 100 μL of the permeabilization buffer 1× (Biolegend, Calif., USA) for 20 minutes. The cells were blocked with species-specific serum (dilution 1:20) for 30 minutes at ambient temperature and were washed with PBS; they were then incubated for one hour with 26.7 μg/mL of the anti-CTLD2 antibody diluted in 1 mL of permeabilization buffer to ensure internalization thereof. The negative control used was the secondary antibody (anti-rat conjugated to phycoerythrin). The cells were washed and incubated with the secondary antibody (1:1000) for one hour. After the cells were washed with PBS, they were resuspended in 100 µL of 4% p-formaldehyde. A total of 10,000 cells for each condition, executed in triplicate, were analyzed on a FACSort (Becton-Dickinson, USA) using the FlowJo software. FIG. 7 shows the intracellular detection of the DEC-205 receptor in Jurkat cells that were permeabilized and stimulated with LPS using the murine monoclonal antibody 2F2E8E3B6 anti-CTLD-2 for detection thereof. The internalization of the DEC-205 receptor was done by stimulation with LPS up to 14% (FIG. 7B) compared to the control (3%) (FIG. 7A). This experiment was carried out in triplicate, where on average 13.5% of cells were observed to present internalization of the antibodies; this indicates that the phenomenon of internalization is indeed taking place.

Example 7

Cloning, Expression, and Purification of Hemagglutinin H5

RNA from the type H5N2 avian flu virus was obtained from a collection of RNAs donated by Dr. R. Webster (St. Jude Hospital, Tennessee, USA). H5 int R, H5 int F, HSR, and H5F oligonucleotides (SEQ ID NO: 9, 10, 11, and 12, respectively) were designed that flanked the hemagglutinin (H5) gene to amplify it by RT-PCR. The gene that codes for hemagglutinin H5 (SEQ ID NO: 8, reported in GenBank with access number gb|ABB88379.1) was cloned in the topo-TA amplification vector (Invitrogen), which was sequenced to confirm the viral origin of the hemagglutinin and to amplify it correctly. This gene was subcloned in the vector pFAST-BacHTb (Invitrogen), which adds six histodines that are contiguous to the amino-terminal region of hemagglutinin H5 ($His_6$-H5) and makes it possible to express it in insect cells. Once the pFAST Bac/H5 plasmid was obtained, it was transformed into DH10-bac cells in which, by double recombination, a recombinant bacmid was obtained that was capable of being transfected into insect cells of the Sf9 (*Spodoptera frugiperda*) and H5 (*Trichopulsia ni*) lines, to be subsequently expressed and purified. After infection for 24, 48, and 72 hours, the infected cells were washed with PBS and collected by centrifuging for 10 minutes at 10,000 RPM. The cells were treated with lysis buffer under native conditions (50 mM $NaH_2PO_4$, 300 mM NaCl, 10 mM imidazole, 1% Nonident P40 and protease inhibitor without EDTA) with incubation for 10 minutes at 4° C. After centrifuging was done, the clarified lysate was subjected to purification by means of Ni-NTA-Agarose affinity chromatography (Qiagen, USA), and the protein of interest was eluted by competency using a concentration gradient of up to 200 mM of imidazole. The $His_6$-H5 protein was monitored by 10% SDS-PAGE and Western-blot (FIG. 8); in the latter case anti-histidine antibodies were used (Pierce, Rockford, Ill., USA).

Figure 8:
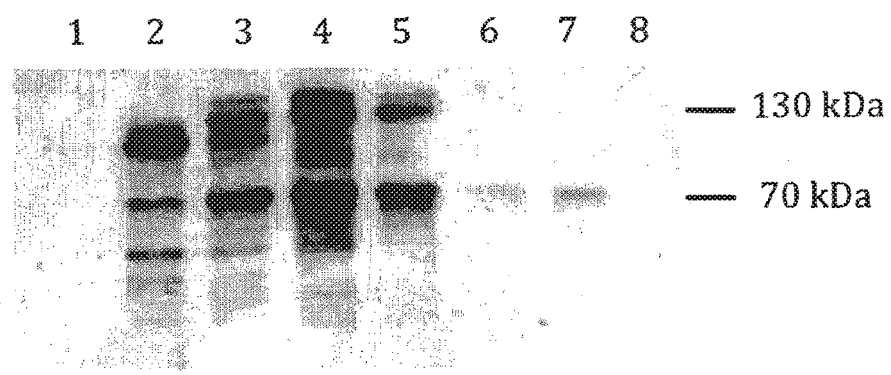

FIG. 8 shows a process of purification of hemagglutinin H5 (SEQ ID NO: 8) using a nickel-NTA-agarose column (Qiagen, USA) and carrying out dilution by competence with increasing concentrations of imidazole. This process was monitored by Western Blot, using anti-histidine antibodies united with peroxidase (Pierce, Rockford, Ill., USA) and revealed with an HRP Luminata Forte substrate (Millipore Corporation, Billerica). Trace 1) material not pegged to the nickel-agarose column; Trace 2) elution 1 with 50 mM of imidazole; Trace 3) elution 2 with 50 mM of imidazole; Trace 4) elution 1 with 100 mM of imidazole; Trace 5) elution 2 with 100 mM of imidazole; Trace 6) elution 1 with 150 mM of imidazole; Trace 7) elution 2 with 150 mM of imidazole; Trace 8) elution 1 with 200 mM of imidazole. Molecular weights of 70 and 130 kDa are noted. It is observed that the hemagglutinin H5 (SEQ ID NO: 8) with a molecular weight of 70 kDa is obtained at homogeneity with elution with 150 mM of imidazole, eliminating dimers and contaminants; this makes it possible to work with it for the subsequent conjugation processes.

Example 8

Chemical Conjugation of Hemagglutinin H5 (SEQ ID NO: 8) of the Avian Flu Virus with Anti-DEC205 Monoclonal Antibodies The anti-CTLD-2 monoclonal antibodies, 2F2E8D3B6, at a concentration of 1 mg/mL, were activated with a 20× molar excess of the cross-linked agent SMCC (succinimidyl-4-(N-maleimidomethyl) cyclohexane-1-carboxylate (SMCC, Pierce, Rockford, Ill., USA) in PBS with 5 mM of EDTA for 2 hours at 4° C. This cross-linking agent contains an NHS ester group and a maleimide group that makes possible the covalent conjugation of the molecules that contain the amino groups and sulfhydryl groups, respectively. After activation, the samples were dialyzed against PBS in order to eliminate the reagent that had been released. On the other hand, the H5 recombinant protein that was obtained in the previous example was modified with 2-iminothiolane (Traut's Reagent, Pierce, Rockford, Ill., USA), which reacts with primary amines in order to add a sulfhydryl group to them. This modification was accomplished by incubating for 1 hour at ambient temperature the protein H5 at a concentration of 14.5 mg/mL in PBS, pH 8.0, with 5 mM of EDTA with a molar excess (10×) of Traut's Reagent, which was prepared at a concentration of 2 mg/mL. After the modification, the sample was dialyzed against PBS in order to eliminate the reagent that had been released. The activated antibodies and the modified protein were incubated for 12 hours at 4° C. in order to ensure covalent coupling thereof.

Example 9

Immunization of Hens with Antibody-Antigen (Anti-DEC-205-Hemagglutinin H5) Complexes Two Rhode Island Red egg-laying hens, 25 weeks old, were immunized with the conjugate Ab 2F2E8D3B6-hemagglutinin H5 that was administered together with lipopolysaccharides (LPS) (SIGMA Aldrich, USA) at a ratio of 2:1. The immunization was given in a single dose of approximately 100 µg of conjugate for each hen, at a volume of 200 µL administered intradermally. The pre-immunization (prior to immunization) eggs and eggs laid during immunization were collected (for a period of 25 days), and they were kept at 4° C. until processed. Purification of the IgYs from the egg yolks was done to determine the titers of the anti-CTLD-2 chicken antibodies by the indirect ELISA method.

Example 10

Extraction, Purification of the IgY Antibodies, and Effect Determination as Modulators of the Immune Response in Chickens of the Antibody-Antigen (Anti-DEC-205 Antibodies-Hemagglutinin H5) Conjugates The eggs of the immunized hens and those used as a control were subjected to manual extraction of the yolks, thus ensuring the release of the membranes that covered them. In general, 15 mL of yolk was obtained for each sample. Then the lipids present in the yolks were removed by separating the aqueous-organic phases using the PBS-chloroform suspension (one volume of chloroform to three volumes of PBS, pH 7.2). The aqueous phase was recovered so that it could be precipitated later with 50% saturated ammonium sulfate, while being stirred continuously and kept at 4° C. overnight. These samples were then centrifuged at 3000×g for 20 minutes at 4° C. in order to obtain the protein precipitate, which was reconstituted in 15 mL of PBS pH 7.2. This material was again precipitated with 30% saturation ammonium sulfate; after the processes of centrifuging and resuspension, all of the samples were subjected to dialysis against PBS pH 7.2, with various buffer changes being made over 24 hours. The concentrations of the proteins extracted from the egg yolks were determined by absorbency at 280 nm. Titration of the anti-hemagglutinin H5 chicken antibodies was done by the indirect ELISA method using 0.3 μg/well of antigen H5 (SEQ ID NO: 8) and a secondary anti-chicken antibody united with peroxidase (dilution 1:2500, Pierce, Rockford, Ill.). The results are presented in FIG. 9, which indicates the IgY titers that recognize hemagglutinin H5 (SEQ ID NO: 8) of the avian flu virus in the two immunized hens on days 15, 18, and 21 post immunization. The hens successfully generated antibodies that were capable of recognizing the viral protein with larger titers than with the control starting on day 15 (titers above 2500) with a single immunization, confirming that the anti-CTLD-2-hemagglutinin H5 conjugates of this invention have the potential to be used as regulators of the immune response in chickens (*Gallus gallus*) to prevent possible viral infections. These results were compared with normal immunization schemes in chickens where in general titers greater than 2000 begin to be obtained as of the fifth week of immunization and after various reinforcement measures (Wen et al., 2012).

Example 11

Recognition of the CTLD2 Domain of DEC 205 in Other Species

In order to analyze whether the antibodies produced recognize the DEC-205 receptor in other species, immunoprecipitation tests were run on species other than chickens (*Gallus gallus*). For this purpose Jurkat cells (the cell line of human T lymphocytes) as well as white cells obtained from the spleens of different animals (pigs and dogs) were lysed in an immunoprecipitation buffer (PBS pH 7.4, 1% Triton X-100 with protease inhibitor). The supernatants of these lysates were incubated with the anti-DEC-205 monoclonal antibodies for 16 hours at 4° C. while being stirred. Then, 50 μL of A-Sepharose protein (Pierce, Rockford, Ill., USA) was used for immunoprecipitation, with incubation being done for one hour at ambient temperature. The immune complexes that were formed were washed extensively. The immunoprecipitates were eluted by boiling for five minutes in a sample buffer with SDS. These precipitates were analyzed on a 10% SDS-PAGE gel under reducing conditions using molecular weight markers. The results are shown in FIG. 10A, where the specific immunoisolation is observed of the DEC-205 receptor (205 kDa) present in Jurkat cells (immortalized line of T lymphocytes) of *Homo sapiens* and white cells of pigs spleens (*Sus scrofa*) in a 10% SDS-PAGE gel under reducing conditions (this was not observed when dog spleen cells were used). The heavy chain (50 kDa) and light chain (25 kDa) of the 2F2E8E3B6 antibody were observed with which the immunoprecipitation was done. The molecular weights are indicated. FIG. 10B shows the alignment of sequences of the CTLD-2 segment of the lymphocytic antigen 75 (DEC-205) of *Gallus gallus* (NP_001032925.1) compared to the sequences of *Homo sapiens* (NP_002340.2) and pig (*Sus scrofa*) (NP_001171875.1), as well as the percentage of identity thereof. It is observed that the two domains exhibit 65% identity compared to the chicken (*Gallus gallus*) domain; this percentage is sufficient to establish the molecular recognition observed in the immunoprecipitation processes.

Example 12

Sequencing of the Variable Regions of the Anti-DEC205 Antibodies

As described in Example 3, the murine antibodies that specifically recognize the CTLD-2 domain of the DEC-205 receptor were purified by means of affinity chromatography with Protein A. The purified antibodies were transferred to nitrocellulose membranes to determine the amino-terminal sequences of the variable regions of the heavy and light chains by means of Edman degradation in a PPSQ-31A sequencer (Shimadzu, Kyoto, Japan). Once this sequence was obtained, the oligos of the amino-terminal regions (SEQ ID NO. 17, 19, 21, and 22) were designed. The oligo is that were used to amplify the carboxyl-terminal regions of the heavy and light chains were taken from specific sites where the constant chains of the two chains began in accordance with the previously obtained isotype; for the case of the light kappa chain, the oligo (SEQ ID NO. 20) reported in Yuan et al., 2004, was used; for the case of the light lambda chain, the oligo (SEQ ID NO. 18) reported in Miller and Glasel, 1989 was used. The oligo for the hinge regions (SEQ ID NO. 23) of the heavy chains was produced in accordance with the consensus sequence of the hinge regions.

The sequences of the regions of the heavy and light chains (VH and VL) of the antibodies originating from the 2F2 and 4D12R hybridomas were identified using the RNA of these hybridomas, which was purified using the "SV Total RNA Isolation" kit (Promega, Madison, USA). The cDNA was obtained by reverse transcription from the RNA using the reverse transcriptase enzyme Expand (Roche Applied Science, Germany). The variable regions were amplified by PCR, where the products were separated on a 1% agarose gel and were purified with the QIAQuick gel extraction kit (Qiagen, USA). These products were ligated using the T4 DNA ligase enzyme (Fermentas, Canada) and were cloned in the cloning vector pBlueScriptks (−) (previously directed with the EcoRV enzyme, Stratagene, USA). The ligation product was transformed into DH5α chemical-competent cells. The transformed cells were plated in petri dishes with YT2X medium fortified with 50 μg/mL of ampicillin, IPTG/XGal for the selection of positive (white) colonies. The cloning of the heavy and light chains was verified by means of colony PCR using the oligos of the vector, T7-like (SEQ ID NO. 24) and T3-like (SEQ ID NO. 25). The colonies having the inserts of the desired sizes (for VH's 750 pb and for VL's 600 pb) were amplified, and the plasmid DNA was purified with the "High Pure Plasmid Isolation" kit (Roche Applied Science, Germany). Then the sequencing of the DNA of the plasmids was done on an Applied Biosystems 3100 gene analyzer (Foster City, Calif., USA). The sequences of the variable regions of the light and heavy chains of the antibody 2F2E8E3B6 (SEQ ID NO. 13 and 15) and of the 4D12R antibody (SEQ ID NO. 14 and 16) were obtained, as was the definition of the complementarity-determining regions (CDRs) of each chain in accordance with the Kabat nomenclature (http://www.bioinf.org.uk/abs/); these are the ones that specifically recognize the CTLD-2 region of the DEC-205 receptor. The heavy ($V_H$) chains present at the $CDR1_H$ of amino acids 26-35,at the $CDR2_H$ of amino acids 50-65, and at the $CDR3_H$ of amino acids 99-103; the light chains present at $CDR1_L$ of amino acids 24-40, at $CDR2_L$ of amino acids 56-62, and at $CDR3_L$ of amino acids 95-102.

The invention claimed is:

1. An isolated antibody that recognizes the CTLD-2 domain of the DEC-205 receptor of *Gallus gallus* (SEQ ID NO. 1), comprising a fragment $V_H$ with an amino acid sequence SEQ ID NO. 15, and a fragment $V_L$ with a sequence SEQ ID NO. 13.

2. A molecular conjugate of the isolated antibody of claim 1 that recognizes the CTLD-2 domain of the DEC-205 receptor of *Gallus gallus*, wherein the antibody is covalently bound to an antigen.

3. The molecular conjugate of claim 2, wherein the antigen is a protein that is selected from the group consisting of proteins from the bacteria *Pasteurella multocida* of avian cholera, *Avibacterium paragallinarum* of infectious avian coryza, the avian viral leucosis virus, and the avian influenza virus.

4. The molecular conjugate of claim 3, wherein the protein used as an antigen is selected from the group consisting of the Cp39 protein of *Pasteurella multocida*, the protein of the HMTp210 external membrane of *Avibacterium paragallinarum*, the gp85 protein of avian leukosis subgroup J, and the H5 protein of the avian influenza virus.

5. The molecular conjugate of claim 4, wherein the conjugate antigen is the H5 protein of the avian influenza virus with amino-acid sequence SEQ ID NO: 8.

6. A veterinary vaccine antigen against avian disease selected from the group consisting of: cholera, avian infectious coryza, avian leukosis subgroup J, and avian influenza, characterized for containing the molecular conjugate of claim 4.

7. A veterinary vaccine antigen against avian influenza, characterized for containing the molecular conjugate of claim 5.

8. A veterinary composition for preventing avian disease, characterized by comprising the molecular conjugate of claim 2, or a salt of said veterinary composition, and an acceptable vehicle.

9. A veterinary composition for preventing avian disease, characterized by comprising the molecular conjugate of claim 3, or a salt of said veterinary composition, and an acceptable vehicle.

10. A veterinary composition for preventing avian disease, characterized by comprising the molecular conjugate of claim 4, or a salt of said veterinary composition, and an acceptable vehicle.

11. A veterinary composition for preventing avian disease, characterized by comprising the molecular conjugate of claim 5, or a salt of said veterinary composition, and an acceptable vehicle.

12. The composition of claim 8, wherein the avian disease is influenza and the molecular conjugate is the H5 protein of the avian influenza virus with amino-acid sequence SEQ ID NO: 8.

13. The composition of claim 9, wherein the avian disease is influenza and the molecular conjugate is the H5 protein of the avian influenza virus with amino-acid sequence SEQ ID NO: 8.

14. The composition of claim 10, wherein the avian disease is influenza and the molecular conjugate is the H5 protein of the avian influenza virus with amino-acid sequence SEQ ID NO: 8.

15. The composition of claim 11, wherein the avian disease is influenza and the molecular conjugate is the H5 protein of the avian influenza virus with amino-acid sequence SEQ ID NO: 8.

* * * * *